US00PP22275P3

(12) United States Plant Patent
Hart

(10) Patent No.: US PP22,275 P3
(45) Date of Patent: Nov. 29, 2011

(54) FEIJOA VARIETY NAMED 'KAITERI'

(50) Latin Name: *Acca sellowiana*
Varietal Denomination: Kaiteri

(76) Inventor: Roy Hart, Mouteka (NZ)

( * ) Notice: Subject to any disclaimer, the term of this patent is extended or adjusted under 35 U.S.C. 154(b) by 155 days.

(21) Appl. No.: 12/322,988

(22) Filed: Feb. 10, 2009

(65) Prior Publication Data

US 2009/0158474 P1 Jun. 18, 2009

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP8,825 P 7/1994 Patterson et al.

OTHER PUBLICATIONS

Anonymous. "Waimea Feijoas" Available at: http://www.waimeanurseries.co.nz/bin/nfdetail.php?code_no=PFG_FSubVarietyDev accessed Jun. 15, 2010.*
Anonymous. "Feijoa Varieties" Available at: http://www.feijoa.org.nz/varieties.html accessed Jun. 15, 2010.*
US Plant Application Serial No. not yet assigned, for Feijoa Varity Named 'Anatoki'.
US Plant Application Serial No. not yet assigned, for Feijoa Varity Named 'Kakariki'.

* cited by examiner

*Primary Examiner* — Wendy C Haas
(74) *Attorney, Agent, or Firm* — Paine Hamblen, LLP

(57) ABSTRACT

A new and distinct variety of feijoa plant *Acca sellowiana* and which is denominated varietally as 'Kaiteri' and which produces a large fruit which is mature for harvesting on or after 4 April under the ecological conditions prevailing near Nelson, New Zealand.

3 Drawing Sheets

Latin name: *Acca sellowiana.*
Varietal designation: 'Kaiteri'.

BACKGROUND OF THE NEW VARIETY

The present invention relates to a new and distinct variety of feijoa '*Acca sellowiana*' and more specifically to a feijoa variety which produces fruit for harvesting in the very early season, that is, from at least about as early as 4 Apr. 2008 under the ecological conditions prevailing near Nelson, New Zealand.

It has long been recognized that it would be desirable to provide a feijoa variety that bears a crop earlier in the season then those varieties that it is most closely similar to and under the ecological conditions prevailing near Nelson, New Zealand. In this regard, several well known and popular feijoa varieties are harvested in both the early and late seasons near Nelson, New Zealand. However, their respective sizes are relatively small, on average, when compared to the very large fruit size produced by the present variety of feijoa. More specifically, the variety of feijoa identified by the varietal name 'Opal Star' (U.S. Plant Pat. No. 8,825) is characterized by producing a relatively small sized fruit (about 85 grams) during the late season, that is, from about 16 May 2008 under the ecological conditions prevailing near Nelson, New Zealand. Still further, the variety 'Apollo' (unpatented), produces an average sized fruit weighing about 100 grams and which is ripe for harvesting about 18 Apr. 2008 under the same ecological conditions. Still further, the unpatented variety 'Triumph' produces a small fruit (about 85 grams) and which is ripe for harvesting about 23 May 2008 under the same ecological conditions. Yet further, the variety 'Unique' (unpatented) also produces a small fruit (about 85 grams), and which is ripe in the early season for harvesting, that is, on or about 18 Apr. 2008 under the ecological conditions prevailing near Nelson, New Zealand. Moreover, the present variety is similar in some respects to the feijoa variety 'Anatoki' (U.S. Patent Pending, Ser. No. 12/378,015), and which is ripe for harvesting in the early season, that is, from about 11 Apr. 2008 under the ecological conditions prevailing near Nelson, New Zealand. Still further, the new variety is somewhat similar to the variety 'Kakariki' (U.S. Patent Pending, Ser. No. 12/378,017), and which produces a large sized fruit (about 100 grams) in the very early season, that is, from about 28 Mar. 2008 under the ecological conditions prevailing near Nelson, New Zealand. In contrast, the present variety 'Kaiteri' is distinguished therefrom and characterized as to novelty by producing a very large sized fruit (about 165 grams) in the very early season, that is, from about 4 Apr. 2008 under the ecological conditions prevailing near Nelson, New Zealand. In view of its early harvesting date, and very large size, the present variety produces a degree of commercial and consumer appeal not present with other known varieties.

ORIGIN AND ASEXUAL REPRODUCTION

The present variety of feijoa was derived from a selective cross-pollination of the unpatented feijoa variety 'Apollo' and an unnamed seedling which was conducted in the cultivated area of the Applicant's farm which is located near Nelson, New Zealand during the 2000 growing season. The present variety 'Kaiteri' was first asexually propagated from cuttings taken from this first asexually reproduced plant. Subsequent thereto, it has been established that the asexually reproduced plants derived from these cuttings are true over successive generations. The present variety is unique and novel as to other varieties with which it is most closely similar to by producing a very large sized fruit having an average weight of about 165 grams and which is ripe for harvesting on or about 4 April under the ecological conditions prevailing near Nelson, New Zealand.

BRIEF DESCRIPTION OF THE DRAWINGS

The accompanying drawings which are provided are color photographs of the new variety of feijoa. The colors in these photographs are as nearly true as is reasonably possible on a color representation of this type. Due to chemical development, processing, and printing, the leaves and fruit depicted in these photographs may or may not be accurate when compared to the actual specimen. For this reason, future color references should be made to the color plates as provided by The Royal Horticulture Society Colour Charts (1995 Edition).

NOT A COMMERCIAL WARRANTY

Figure 1:
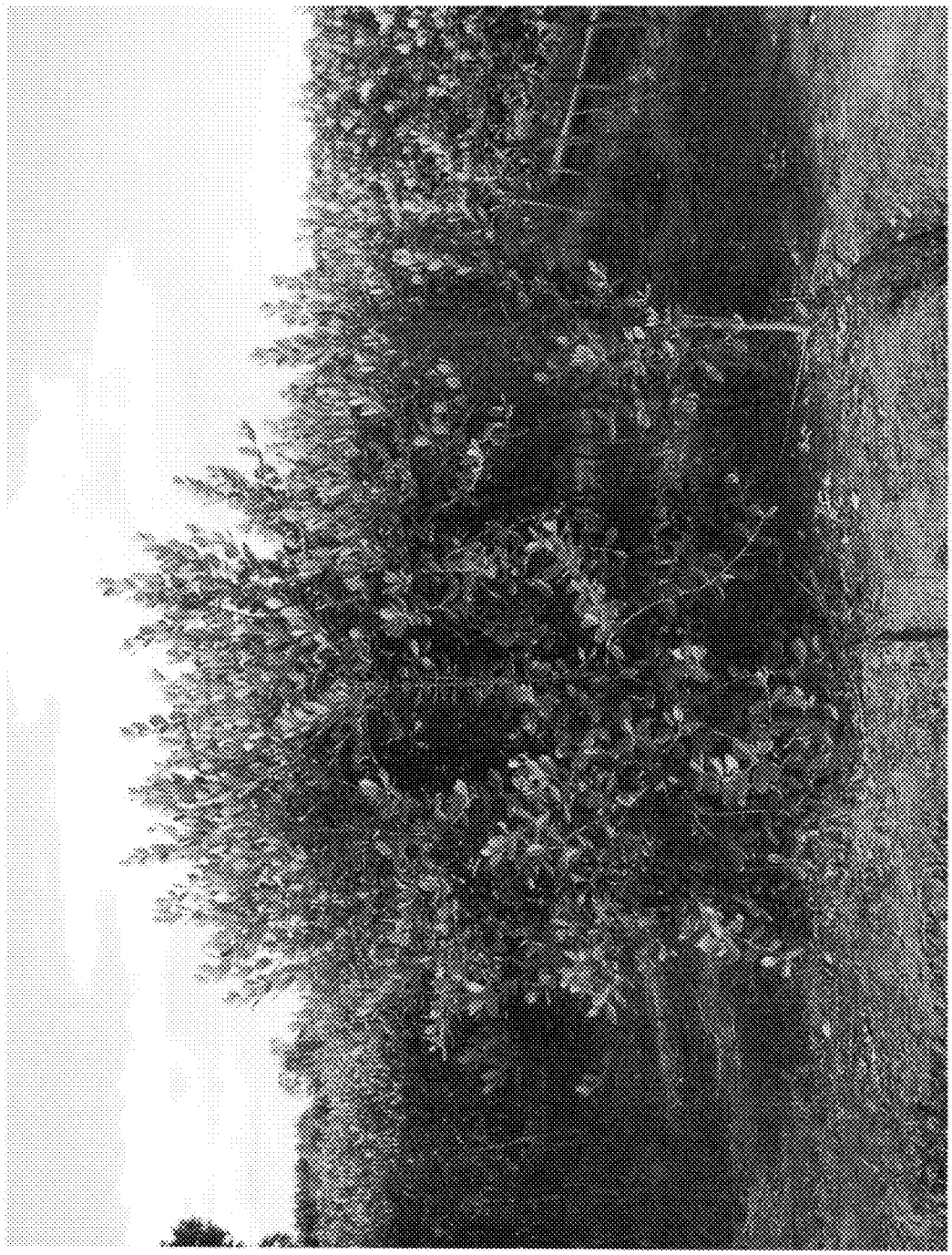
FIG. 1 is a color photograph depicting the new variety of feijoa growing on its own roots and which is approximately 4 years old.
Figure 2:
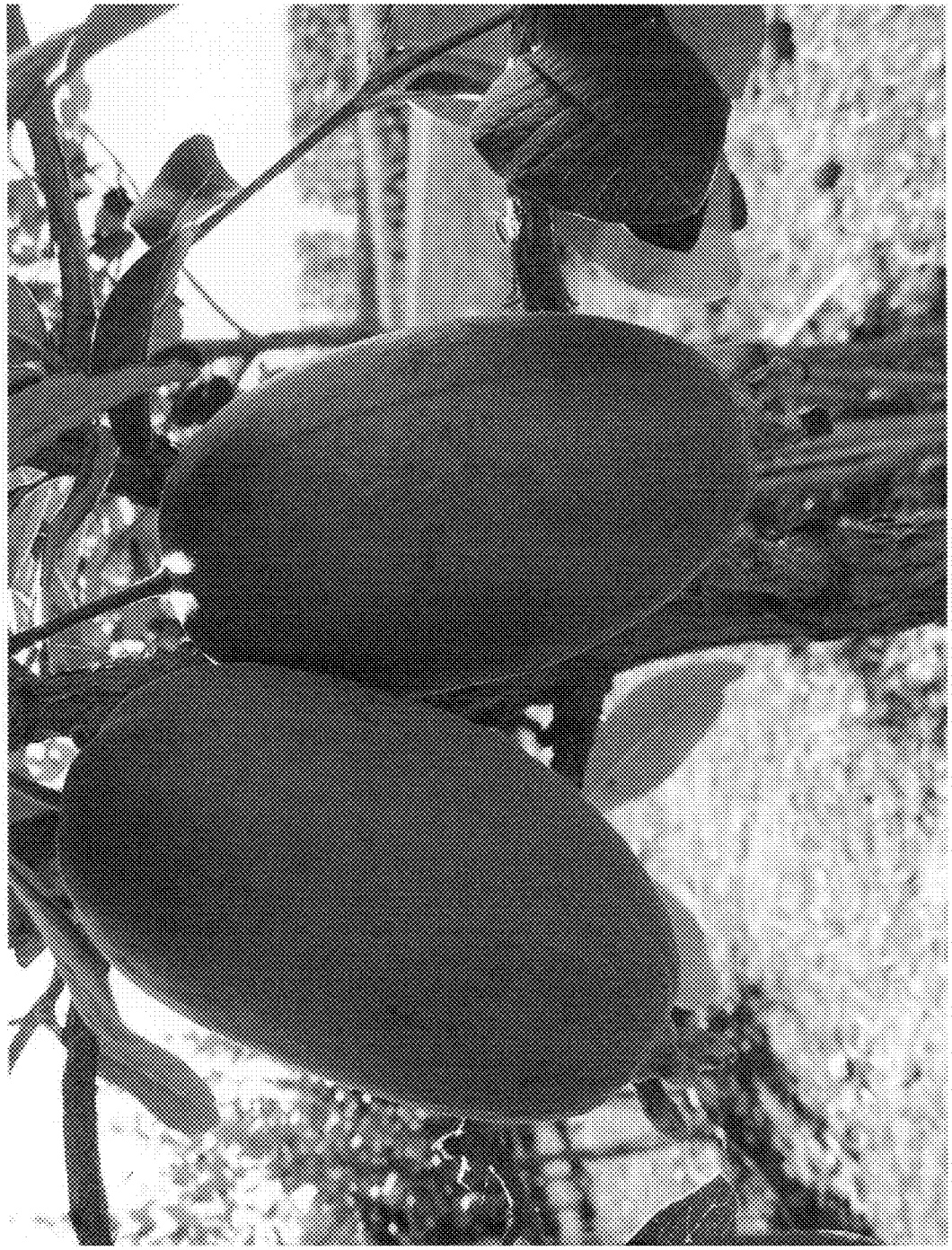
FIG. 2 is a photograph of two fruit that are sufficiently matured for harvesting.
Figure 3:
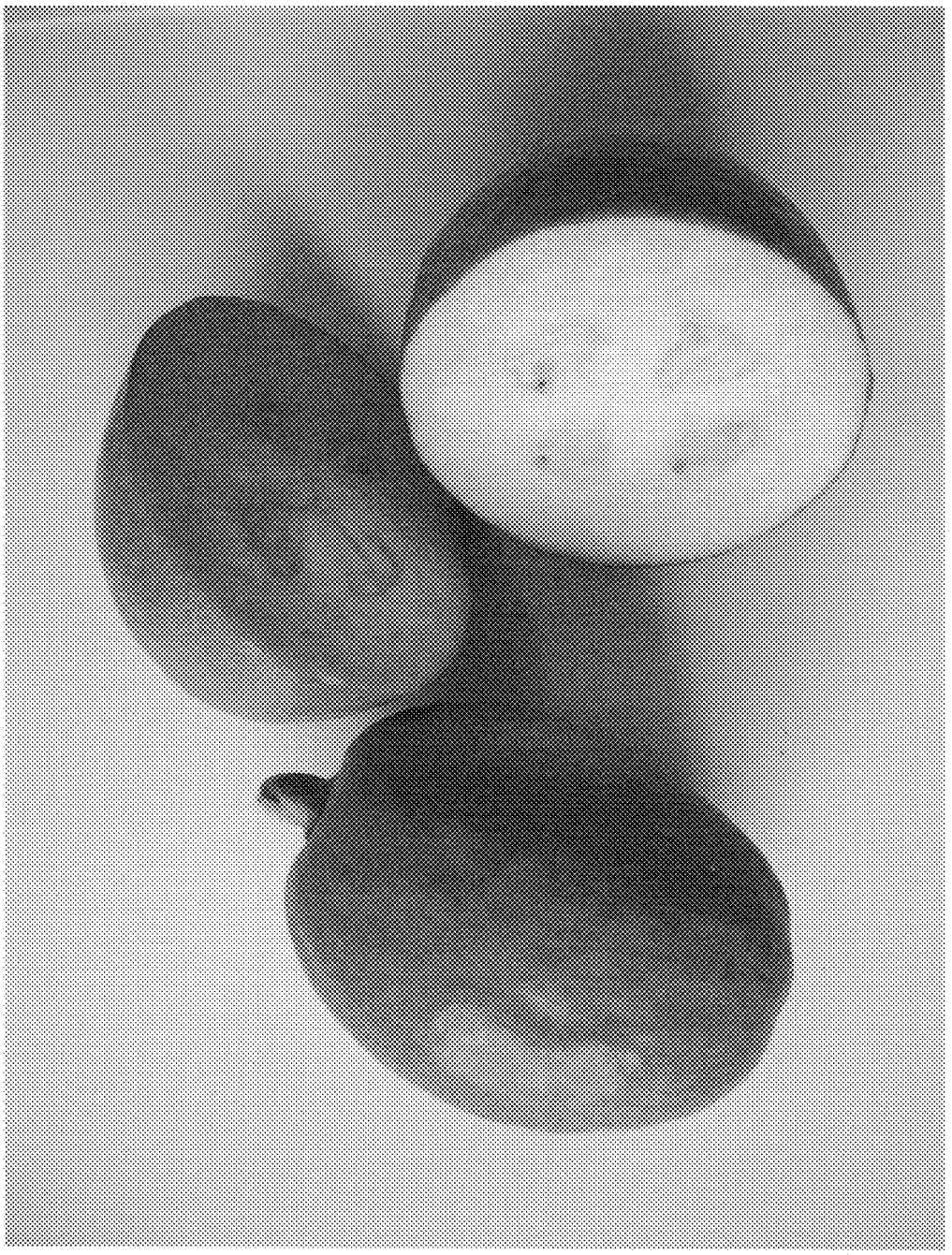
FIG. 3 is a photograph of two fruit which have been harvested, one of which has been divided in the equatorial plane and which shows the flesh characteristics thereof.

The following detailed description has been prepared to solely comply with the provisions of 35 USC §112, and does not constitute a commercial warranty (either expressed or implied), that the present variety will, in the future, display the botanical or other varietal characteristics as set forth in this application. Therefore, this disclosure may not be relied upon to support any future legal claims, which include, but are not limited to breach of warranty of merchantability, fitness for any particular purpose, or non-infringement which is directed in whole, or in part, to the present variety.

DETAILED DESCRIPTION

Tree:

*Vigor.*—Considered average for the species.
*Tree form.*—Ramified.
*Growth habit.*—Considered spreading.
*Tree size.*—Height — About 2 meters.
*Tree crown.*—Size — About 2 meters when measured at a height of about 1 meter above the ground.

Trunk:

*Diameter.*—About 7 cm. when measured at a distance of about 20 cm. about the ground.
*Bark texture.*—Rough and somewhat flaky.
*Bark color.*—Grey-brown (RHS 199B).

Leaves:

*Leaf length.*—On average about 70 mm.
*Leaf width.*—On average about 35 mm.
*Leaf shape.*—Generally — Considered elliptical.
*Marginal form.*—Straight.
*Leaf color.*—Upper Surface — Green (RHS 139A).
*Leaf color.*—Lower Surface — Grey-green (RHS 190C).

Flowers:

*Quantity of flowers per cluster.*—4 or 5 flowers may be found per cluster.
*Flower petals.*—Quantity — 4.
*Flower petal color.*—Upper Surface — White (RHS 155C).
*Flower petal color.*—Lower Surface — Red-purple (RHS 65D).
*Sepals.*—Quantity — Typically 4 are found.
*Stamins.*—Quantity — Numerous.
*Stamins.*—Color — Red (RHS 45C).
*Pistil.*—Quantity — 1.
*Pistil.*—Color — Red (RHS 45A).
*Pollination.*—Generally — Self-infertile. The inventor has discovered that any other feijoa variety that flowers at approximately the same time of the season is a suitable pollinator.

Fruit:

*Fruit size.*—Generally — Considered very large. On average the fruit of the present variety weighs about 165 grams.
*Fruit length.*—About 90 mm.
*Fruit width.*—About 60 mm.
*Fruit form.*—Considered elongated and obovoid when considered in profile.
*Skin texture.*—Considered smooth.
*Skin color.*—Yellow-green (RHS 144B).
*Flesh texture.*—Considered smooth and soft.
*Flesh flavor.*—Sweet with some hint of acid. The flesh is aromatic.
*Brix.*—Approximately 12 degrees at harvest.
*Flesh color.*—Yellow-green (RHS 150D).
*Date of maturity.*—Very early under the ecological conditions prevailing near Nelson, New Zealand, that is, on or after 4 Apr. 2008.
*Fruit use.*—Primarily for fresh and processed consumption.
*Keeping quality.*—About 16 days at 1 degree Celsius. The fruit has an approximate 2 to 7 day shelf life.

Although the new variety of feijoa possess the described characteristics when grown under the ecological conditions prevailing near Nelson, New Zealand, it should be understood that variations of the usual magnitude and characteristics incident to changes in growing conditions, fertilization, pruning and pest control are to be expected.

Having thus described and illustrated my new variety of feijoa, what we claim is new, and desire to secure by plant Letters Patent is:

1. A new and distinct variety of feijoa plant substantially as illustrated and described and which is characterized principally as to novelty by bearing a very large fruit which is mature for harvesting on or after 4 April under the ecological conditions prevailing near Nelson, New Zealand.

* * * * *